United States Patent [19]

Mount et al.

[11] 4,337,174

[45] Jun. 29, 1982

[54] METHOD FOR PREPARING A CATALYST AND INTERMEDIATE FORMED THEREBY

[75] Inventors: Ramon A. Mount; Harold Raffelson, both of St. Louis, Mo.

[73] Assignee: Monsanto Company, St. Louis, Mo.

[21] Appl. No.: 232,441

[22] Filed: Feb. 2, 1981

Related U.S. Application Data

[63] Continuation of Ser. No. 73,480, Sep. 7, 1979, abandoned, which is a continuation-in-part of Ser. No. 698,458, Jun. 21, 1976, abandoned.

[51] Int. Cl.³ .............................................. B01J 27/18
[52] U.S. Cl. ..................................... 252/437; 252/435
[58] Field of Search .................. 252/435, 437; 423/305

[56] References Cited

U.S. PATENT DOCUMENTS

| | | | |
|---|---|---|---|
| B 330,354 | 1/1975 | Mount, et al. | 252/437 |
| 3,293,268 | 12/1966 | Bergman et al. | 252/437 X |
| 3,864,280 | 2/1975 | Schneider | 252/435 X |

*Primary Examiner*—Patrick Garvin
*Attorney, Agent, or Firm*—Thomas Y. Awalt, Jr.

[57] ABSTRACT

In conventional procedures for the preparation of phosphorus-vanadium-oxygen catalysts, with or without promoting elements or carriers, the phosphorus compounds and vanadium compounds are mixed under conditions to form precursors. These precursors are then heated to temperatures up to 600° C. to form phosphorus-vanadium-oxygen catalysts suitable for the conversion of saturated hydrocarbons, such as butane, to maleic anhydride. By the process of the present invention, a new phosphorus-vanadium-oxygen composition is formed which is converted to the precursor. Catalysts formed by the process of the present invention, when used for the conversion of saturated hydrocarbons to maleic anhydride, provide higher yields of maleic anhydride.

8 Claims, No Drawings

METHOD FOR PREPARING A CATALYST AND INTERMEDIATE FORMED THEREBY

CROSS-REFERENCE TO RELATED APPLICATION

This application is a continuation of application Ser. No. 73,480, filed Sept. 7, 1979 and now abandoned, which in turn is a continuation-in-part of our application, Ser. No. 698,458 filed June 21, 1976 and now abandoned.

BACKGROUND OF THE INVENTION

This invention relates to a method for preparing catalysts useful in the manufacture of maleic anhydride by the oxidation of hydrocarbons. More particularly, it is directed to the preparation of catalysts suitable for producing maleic anhydride from saturated hydrocarbons.

Maleic anhydride is of significant commercial interest throughout the world. It is used alone or in combination with other acids in the manufacture of alkyd and polyester resins. It is also a versatile intermediate for chemical synthesis. Significant quantities of maleic anydride are produced each year to satisfy these needs.

The prior art teaches that vanadium catalysts are well suited to the production of maleic anhydride from hydrocabons, and further, that vanadium catalysts wherein the valence of the vanadium is between about 3.8 and 4.8 are particularly well suited for the production of maleic anydride from saturated hydrocarbons. The prior art further teaches that phosphorus-vanadium-oxygen catalysts are particularly useful for the conversion of aliphatic hydrocarbons to maleic anhydride and discloses a number of ways of preparing such catalysts.

Many prior art procedures for the preparation of phosphorus-vanadium-oxygen catalysts teach that it is preferable to reduce the vanadium in solution to the tetravalent state. For example, these catalysts can be prepared by contacting phosphorus compounds and vanadium compounds under conditions to form the tetravalent vanadium and to form the catalyst precursor, and thereafter, calcining the resultant phosphorus-vanadium-oxygen compound.

Although the prior art procedures provide acceptable catalysts, it has now been found that a superior performing catalyst can be prepared by the process of the present invention.

SUMMARY OF THE INVENTION

According to the present invention, a method of preparing a catalyst is provided which comprises: (A) bringing together in a reaction zone a phosphorus compound and a vanadium compound in a phosphorus to vanadium atom ratio between about 0.8:1 and about 1.5:1 under acidic conditions to dissolve the reactant compounds and to provide at least 50 atom percent tetravalent vanadium and to form a phosphorus-vanadium-oxygen complex; (B) heating the complex at a temperature between about 60° C. and about 120° C. for a period of time sufficient to form and precipitate an intermediate compound; (C) heating the intermediate compound at a temperature above about 130° C. to form a catalyst precursor; and thereafter, (D) calcining the catalyst precursor at a temperature between about 300° C. and about 600° C. In one embodiment of this invention, a dispersion is formed which comprises the intermediate compound dispersed in an acidic medium. The intermediate compound is an oxide composition, which comprises phosphorus, vanadium and oxygen, having a unique X-ray diffraction pattern.

For the purpose of this invention, the term "yield" means the ratio of the moles of maleic anhydride obtained to the moles of hydrocarbon feed introduced into the reaction. The term "space velocity" means the hourly volume of gaseous feed expressed in cubic centimeters (cc) at 15.5° C. and standard atmospheric pressure, divided by the catalyst bulk volume expressed in cubic centimeters (cc), the term expressed as cc/cc/hour.

The catalysts of this invention are particularly useful for converting aliphatic hydrocarbons, both saturated and unsaturated, to maleic anhydride and the catalysts of this invention are particularly useful for the conversion of a saturated hydrocabon, such as butane, to maleic anhydride. The catalysts are prepared by a method which provides a phosphorus-vanadium-oxygen intermediate compound having a unique X-ray diffraction pattern. This intermediate compound is not obtained by prior art methods and is believed to be responsible for the improved performance of the catalysts made according to the method of the present invention. Details of the catalyst preparation, the X-ray diffraction peaks of the intermediate compound and catalyst precursor, and the use of the catalysts made via the intermediate compound to convert saturated hydrocarbons to maleic anhydride are hereinafter described.

PREPARATION OF THE CATALYSTS

Broadly described, the phosphorus-vanadium-oxygen catalysts having improved performance, according to the present invention, are prepared by contacting vanadium compounds and phosphorus compounds under acidic conditions to provide a substantial amount, i.e., at least 50 atom percent, of tetravalent vanadium and to form a phosphorus-vanadium-oxygen complex having a phosphorus to vanadium atom ratio between about 0.8:1 and about 1.5:1. The complex is heated at a temperature between about 60° C. and about 120° C. for a period of time, usually about 24 hours or more, sufficient to form and precipitate an intermediate compound having a unique X-ray diffraction pattern hereinafter described. The intermediate compound is then heated at a temperature above about 130° C. to form a catalyst precursor. Thereafter the catalyst precursor is calcined at a temperature between about 300° C. and about 600° C. to form catalysts.

The vanadium compounds useful in the process of the present invention are those known to the art. Suitable vanadium compounds include: vanadium oxides, such as vanadium pentoxide, vanadium tetroxide, vanadium trioxide, and the like; vanadium oxyhalides, such as vanadyl chloride, vanadyl dichloride, vanadyl trichloride, vanadyl bromide, vanadyl dibromide, vanadyl tribromide, and the like; vanadium acids, such as metavanadic acid, pyrovanadic acid, and the like; and vanadium salts, such as ammonium metavanadate, vanadium sulfate, vanadium phosphate, vanadyl formate, vanadyl oxalate, and the like. However, vanadium pentoxide is preferred.

As a source of phosphorus for use in preparing the catalysts made by the process of the present invention, useful phosphorus compounds are also those that are known in the art. Suitable phosphorus compounds, include: Phosphoric acid, such as metaphosphoric acid, orthophosphoric acid, triphosphoric acid, pyrophosporic acid, and the like; phosphorus pentoxide, and the like; phosphorus halides, such as phosphorus oxyiodide, phosphorus pentachloride, phosphorus oxybromide, and the like; organophosphorus compounds, such as ethylphosphate, methylphosphate, and the like; and trivalent phosphorus compounds, such as phosphorous acid, phosphorus trichloride, phosphorus tribromide or organic phosphites, sometimes known as phosphonates, of the type such as trimethyl phosphite, triethyl phosphite, tripropyl phosphite, and the like. Mixtures of these phosphorus compounds can also be used. However, phosphoric acid, phosphorous acid and phosphorus pentoxide are preferred, and it is especially preferred to use a mixture of phosphoric acid or phosphorus pentoxide and phosphorous acid.

Numerous techniques are known to those skilled in the art for bringing together in a reaction zone a phosphorus compound and a vanadium compound under conditions to provide at least 50 atom percent tetravalent vanadium, and to form a phosphorus-vanadium-oxygen complex. For example, a vanadium compound is heated with a phosphorus compound and a reducing agent in an acid solution to dissolve the starting materials and reduce any pentavalent vanadium to tetravalent vanadium, and to maintain the vanadium in the tetravalent state. It has been found that the intermediate compound of the present invention will not form readily when hydrohalide acid, such as hydrochloric acid, is used to provide acidic conditions even though the art teaches that a hydrohalide acid can serve to provide an acidic medium and as a reducing agent for pentavalent vanadium in the preparation of such catalysts. Although Applicants do not wish to be bound by any particular theory, it is believed that a large amount of hydrogen halide prevents the formation and precipitation of the intermediate compound of the present invention. It is preferred to use a phosphorus-vanadium-oxygen complex that is essentially hydrogen halide-free to prepare the phosphorus-vanadium-oxygen intermediate compound of this invention. As is known to those skilled in the art, organic compounds which are known to be mild reducing agents, such as formaldehyde and the like, can be added to the acidic solution of the reactant compounds to reduce the vanadium and to maintain the vanadium in the tetravalent state. On the other hand, oxalic acid or phosphoric acid, which are mild reducing agents, can serve not only as the acidic medium but also serve as the reducing agent for the pentavalent vanadium, and these acids are preferred in the process of the present invention.

The acidic medium containing the phosphorus compound and the vanadium compound is heated until a blue solution is obtained indicating that a substantial amount, i.e., greater than 50 atom percent, of the vanadium is in the tetravalent state. The amount of time required to dissolve the phosphorus and vanadium compounds and to reduce a substantial amount of the vanadium to the tetravalent state to form an intermediate oxide complex varies from batch to batch depending upon the compounds used as starting materials and the temperature at which the copounds are heated. Generally, the color of the solution changes to dark blue, indicating that a substantial amount of the vanadium is in the tetravalent state. However, as will occur to those skilled in the art, an aliquot of the solution can be analyzed to insure that most of the vanadium is in the tetravalent state.

Although any number of phosphorus compounds and vanadium compounds can be used to form the phosphorus-vanadium-oxygen complex, the atom ratio of phosphorus to vanadium in the complex is important since it controls the phosphorus to vanadium atom ratio in the final catalyst. When the phosphorus to vanadium atom ratio is below about 0.8:1 or above about 1.5:1, the yield of maleic anhydride using the catalyst prepared by the process of the present invention is so low that it is not of commercial significance. It is preferred to maintain the phosphorus to vanadium atom ratio between about 1:1 and 1.2:1, say about 1.05:1.

The prior art generally discloses that the phosphorus compound and the vanadium compound are brought together in a reaction zone, the compounds are dissolved and substantially all the vanadium is reduced to the tetravalent state, and the solution is then heated to form a phosphorus-vanadium-oxygen precursor which is then calcined to form the catalyst. However, it is critical in the process of this invention to employ an intermediate controlled heating of the solution at a temperature between about 60° C. and about 120° C. for a period of time sufficient to form and precipitate an intermediate compound having a unique X-ray diffraction pattern as hereinafter disclosed. It has been found that heating the initial phosphorus, vanadium and oxygen complex at a temperature above about 120° C. prevents the formation of the intermediate compound which is necessary to form the catalysts according to the process of the present invention. At temperatures below about 60° C., the formation of the intermediate compound is so slow that it requires extended periods of time to form. It is preferred to heat the initial complex at a temperature between about 90° C. and about 100° C., say about 95° C.

The length of time that the initial complex is heated to form the intermediate compound can vary within wide ranges, but it has been found that at least about 24 hours of heating is required to form the intermediate compound. In some cases, heating as long as 120 hours may be necessary to form and precipitate the intermediate compound. It is preferred to heat the initial complex for at least 36 hours and sometimes as long as 72 hours at temperatures between about 90° C. and about 100° C., to insure the precipitation of the intermediate compound.

After the intermediate compound has been formed, it is then heated to a temperature above about 130° C., and preferably from about 130° C. to about 170° C. for a period of time between about 2 and about 4 hours, to form a catalyst precursor. It is even more preferred to heat the intermediate compound in a closed vessel, such as a stirred autoclave, to a temperature between about 140° C. and 160° C. to form a phosphorus-vanadium-oxygen catalyst precursor.

After the catalyst precursor has been formed, it is then calcined at temperatures between about 300° C. and about 600° C. to form a phosphorus-vanadium-oxygen catalyst. Techniques for calcining the catalyst precursor are known to those skilled in the art, and the catalyst precursor can be calcined in an inert gas or in air, or even in the presence of a mixture of a hydrocarbon and air, to form a suitable catalyst. After the phosphorus-vanadium-oxygen catalyst precursors have been calcined to form a phosphorus-vanadium-oxygen catalyst, the catalysts can be used to convert aliphatic hydrocarbons to maleic anhydride. However, the initial yield of maleic anhydride may be low, and if this is the case, the catalysts can be "conditioned" as will occur to those skilled in the art, by passing low concentrations of aliphatic hydrocarbon-in-air at low space velocities through the catalysts for a perid of time before production operations begin.

THE INTERMEDIATE

In the preferred method of preparing the intermediate compound of this invention, a phosphorus compound and a vanadium compound are brought together in a reaction zone in an aqueous acid medium under conditions to provide at least 50 atom percent tetravalent vanadium and to form a phosphorus-vanadium-oxygen complex having a phosphorus to vanadium atom ratio between about 1:1 and 1.2:1. Thereafter the complex is heated at a temperature between about 90° C. and about 100° C. for a period of time between about 24 hours and about 72 hours, until the intermediate compound precipitates and a dispersion of the intermediate compound dispersed in the reaction medium is formed. The intermediate compound is an oxide composition comprising phosphorus, vanadium and oxygen having the following major X-ray diffraction peaks measured using CuKa radiation in a General Electric X-ray Diffractometer, Model 5;

| °2 theta (CuKα) | Relative Intensity | d-spacing |
|---|---|---|
| 13.20 | 100 | 6.70 |
| 15.60 | 40 | 5.68 |
| 26.70 | ~30 | 3.34 |
| 28.25 | 95 | 3.16 |
| 28.85 | 30 | 3.09 |

As will occur to those skilled in the art, the total dispersion will have a phosphorus to vanadium atom ratio between about 0.8:1 and about 1.5:1, and preferably between about 1:1 and about 1.2:1. However, the intermediate compound will have a phosphorus to vanadium atom ratio of about 1:1.

The catalyst precursor is an oxide composition comprising phosphorus, vanadium and oxygen having the following major X-ray diffraction peaks measured using CuKa radiation in a General Electric X-ray Diffractometer, Model 5:

| °2 theta (CuKα) | Relative Intensity | d-spacing |
|---|---|---|
| 15.40 | 100 | 5.75 |
| 19.60 | 100 | 4.52 |
| 21.70 | 10 | 4.10 |
| 24.20 | 60 | 3.68 |
| 27.10 | 50 | 3.29 |
| 28.70 | 20 | 3.11 |
| 30.40 | 70 | 2.94 |
| 32.10 | 20 | 2.79 |
| 33.70 | 30 | 2.66 |

Difference between the intermediate compound of this invention and the normal precursor is seen from comparison of the above X-ray diffraction patterns of the two compounds.

PREPARATION OF MALEIC ANHYDRIDE

After the intermediate compound is converted to the phosphorus-vanadium-oxygen catalyst precursor, and the catalyst precursor has been calcined, the catalyst thus formed is placed in a reactor used to convert hydrocarbons to maleic anhydride. Thereafter, a hydrocarbon and air mixture can be passed through the catalyst to produce maleic anhydride.

The catalysts of the present invention are useful in a variety of reactors to convert hydrocarbons to maleic anhydride. Both fluidized bed reactors and fixed tube heat exchanger type reactors are satisfactory and the details of the operation of such reactors are well known to those skilled in the art. The reaction to convert hydrocabons to maleic anhydride requires only passing the hydrocarbons admixed with a free-oxygen containing gas, such as air or oxygen-enriched air, through the catalyst at elevated temperatures. The hydrocarbon-air mixture is passed through the catalysts at a concentration of about 1 to about 10 mole percent hydrocarbon at a space velocity of about 100 to 3,000 cc/cc/hour and at temperatures between about 350° C. and about 600° C. to provide high maleic anhydride yields.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

A large number of non-aromatic hydrocarbons having from 4 to 10 carbon atoms can be converted to maleic anyhydride using the catalysts of the present invention. It is only necessary that the hydrocarbon contain not less than 4 carbon atoms in a straight chain. As an example, the preferred saturated hydrocarbon is butane, but isobutane which does not contain 4 carbon atoms in a straight chain, is not satisfactory for conversion to maleic anhydride, although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the saturated hydrocarbons, unsaturated hydrocarbons can be used. The preferred unsaturated hydrocarbon is butene, but other unsaturated hydrocarbons within the scope of this invention include butadiene, the pentenes, the hexenes, the heptenes, the octenes, the nonenes, the decenes or mixtures of any of these with or without butene. Cyclic compounds such as cyclopentane or cyclopentane or oxygenated compounds such as furan, dihydrofuran, or even tetrahydrofurfural alcohol are satisfactory. Furthermore, the aforementioned feed stocks are not necessarily pure substances, but can be technical hydrocarbons.

DESCRIPTION OF THE PREFERRED EMBODIMENTS

This invention is illustrated by, but not limited to, the following Examples.

EXAMPLE 1

This Example illustrates the preparation of the intermediate compound in the preparation of a catalyst according to this invention.

Into a 3-liter round bottomed flask equipped with a stirrer and a reflux condenser was placed 595 grams of vanadium pentoxide, 285.6 grams of 96.8 percent phosphorous acid, 403.6 grams of 85 percent phosphoric acid, and 2012.5 grams of deionized water. The phosphorus to vanadium atom ratio was about 1.05:1, and contained about 3 percent more phosphorous acid than the stoichiometric amount required to reduce the pentavalent vanadium to the tetravalent state. The mixture was heated at reflux conditions until the solution turned blue. Thereafter, heating was continued at a temperature of about 97° C. to 99° C. A pale blue-green precipitate was formed after 24 hours, forming a dispersion in the water and dissolved phosphorus and vanadium compounds. Heating was continued for about another 28 hours.

Analysis of a sample of the precipitate indicated that it was an oxide composition comprising phosphorus, vanadium and oxygen having major X-ray diffraction peaks at °2 theta using CuKα radiation in a General Electric X-ray Diffractometer, Model 5, as follows:

| d-spacing |
|---|
| 6.70 |
| 5.68 |
| 3.34 |
| 3.16 |
| 3.09 |

EXAMPLE 2

This Example illustrates the preparation of the catalyst by forming the catalyst precursor from the intermediate compound of Example 1.

About 1895 grams of the material from Example 1 was transferred to a 2-liter autoclave along with about 250 milliliters of deionized water. The autoclave was closed and heated to about 150° C. for about 4 hours. After cooling, the autoclave was opened and the contents transferred to open dish casseroles and evaporated to dryness at 120° C. in a forced draft oven. A sample of the dried powder (catalyst precursor) was analyzed by X-ray diffraction analysis according to the procedure of Example 1 which indicated that it was an oxide composition comprising phosphorus, vanadium and oxygen having major X-ray diffraction peaks, as follows:

| d-spacing |
|---|
| 5.75 |
| 4.52 |
| 4.10 |
| 3.68 |
| 3.29 |
| 3.11 |
| 2.94 |
| 2.79 |
| 2.66 |

The dried powder was ground to pass an 18 mesh screen, admixed with 1 weight percent graphite, and pressed into 3/16-inch (~0.48 cm) diameter tablets. The tablets were then placed in an oven and heated to about 400° C. for about 6 hours. Thereafter, the oven was allowed to cool for 1 hour, and the calcined tablets were removed. The tablets were charged to a 2.1 cm (0.83 in) internal diameter, iron, fixed-tube reactor. A hydrocarbon-air mixture containing 2.0 mole percent butane was contacted with the catalyst at a space velocity of about 1470 cc/cc/hour. Maleic anhydride was obtained at a 52.3 percent yield after 103 hours at a temperature of about 404° C. The results obtained using this reactor correlate well with results that would be obtained in a production reactor.

EXAMPLE 3

This example illustrates the preparation of the catalyst by forming the catalyst precursor directly, bypassing the formation and precipitation of the intermediate compound.

Into a 2-liter autoclave was charged 340 grams of vanadium pentoxide, 215 grams of 85% phosphoric acid, 173 grams of 97% phosphorous acid and 1150 grams of deionized water. The mixture was stirred and heated at 145°–150° C. for 2 hours. The phosphorus to vanadium atom ratio was about 1.05:1. After cooling, the autoclave was opened and the contents transferred to open dish casseroles, evaporated to dryness and heated overnight at 120° C. in a forced draft oven. A sample of the dried material was analyzed by X-ray diffraction analysis according to the procedure set forth in Example 1 and found to have the same major peaks as the precursor of Example 2. The dried material was ground to pass an 18 mesh screen, admixed with 1 weight percent graphite, and pressed into 3/16-inch (~0.48 cm) diameter tablets. The tablets were calcined under the same conditions as set forth in Example 2 above. Using the laboratory reactor as set forth in Example 2 above, the catalyst was contacted with a hydrocarbon-air mixture containing 2.0 mole percent butane at a space velocity of 1460 cc/cc/hour. The yield of maleic anhydride was 51.1 percent after 216 hours at a temperature of 412° C. At a temperature of 404° C. the maleic anhydride yield was 49.1 percent after 210 hours.

EXAMPLE 4

This Example illustrates the preparation of the catalyst directly from the intermediate compound, bypassing the formation of the catalyst precursor.

Into a 500 milliliter round-bottomed flask equipped with a stirrer and reflux condenser was added 84.6 grams of vanadium pentoxide, 70.4 grams of oxalic acid dihydrate and 282 milliliters of deionized water. Thereafter, 112.6 grams of 85% phosphoric acid was added in small portions over a 2-hour period. The phosphorus to vanadium atom ratio was about 1.05:1. The contents in the flask was heated at reflux conditions until a dark blue solution was obtained, indicating the presence of tetravalent vanadium. A precipitate formed after heating was continued for about 92 hours at a temperature of about 97° C. The contents of the flask was poured into an evaporating dish and heated at 120° C. in a forced draft oven overnight. A sample of the resulting solids was analyzed by X-ray diffraction analysis according to the procedure set forth in Example 1 and found to have the same major peaks as the precipitate (intermediate compound) of Example 1. The solids were wet with water to make a paste which was extruded through a 7/32-inch (0.54 cm) die. The extrudate was cut into 7/32-inch lengths and calcined by heating at 500° C. for 4 hours. Using the laboratory reactor as set forth in Example 2 above, the catalyst was contacted with a hydrocarbon-air mixture containing 1.5 mole percent butane at a space velocity of 1340 cc/cc/hour. The yield of maleic anhydride was 39.0% after 42 hours at a temperature of 416° C.

EXAMPLE 5

This Example illustrates the use of formaldehyde as the reducing agent in the formation of the intermediate compound according to this invention.

Into a 500 milliliter round-bottomed flask equipped with a stirrer and a reflux condenser was added 50 grams of vanadium pentoxide, 66.6 grams of 85% phosphoric acid, 67.2 grams of formaldehyde (36% in water) and 141 milliliters of deionized water. The mixture was heated at reflux conditions until the solution turned blue, indicating the presence of tetravalent vanadium. The phosphorus to vanadium atom ratio was about 1.05:1. Heating was continued for about 32 hours until a thick precipitate of the pale-green intermediate in water was observed. The contents of the flask were transferred to an evaporating dish and heated at 120° C. in a forced draft oven overnight. A sample of the resulting solids was analyzed by X-ray diffraction analysis according to the procedure set forth in Example 1 and found to have the same major peaks as the intermediate compound of Example 1.

EXAMPLE 6

This Example illustrates preparation of catalyst according to the prior art using hydrochloric acid as the acid media and reducing agent.

Into a 12 liter round-bottomed flask equipped with a stirrer and reflux condenser was added 754.1 grams of vanadium pentoxide, 1001.3 grams of 85% phosphoric acid and 8430 cc of 37% hydrochloric acid. The phosphorus to vanadium atom ratio was about 1.05:1. The mixture was stirred and heated at 90° C. for 90 minutes and then stripped of 6990 cc of material. The remaining material was placed in a casserole on a steam bath and dried. A sample of the resulting solids was analyzed by X-ray diffraction analysis according to the procedure set forth in Example 1 and found to have the same major peaks as the catalyst precursor of Example 2. The solids were screened to 60 mesh and wet with water to make a paste which was extruded through a 7/32 inch (0.54 cm) die. The extrudate was cut into 7/32-inch lengths and calcined for 4 hours at 500° C. Using the laboratory reactor as set forth in Example 2 above, the catalyst was contacted with a hydrocarbon-air mixture containing 1.5 mole percent butane at a space velocity of 1370 cc/cc/hour. The yield of maleic anhydride and 45.6% after 130 hours at a temperature of 438° C.

EXAMPLE 7

This Example illustrates the preparation of extruded catalysts using phosphoric acid as the acid media and reducing agent with the precursor formed directly, bypassing the formation of the intermediate.

Into a 2-liter autoclave was charged 340.0 grams of vanadium pentoxide, 215.5 grams of 85% phosphoric acid, 168.6 grams of 100% phosphorous acid and 1150 grams of deionized water. The mixture was stirred and heated to 145°–147° C. for 4 hours. After cooling, the autoclave was opened, the contents transferred to an open dish casserole and evaporated to dryness at a temperature of 120° C. A sample of the resulting powder was analyzed by X-ray diffraction analysis according to the procedure in Example 1 and found to have the same major peaks as the catalyst precursor of Example 2. The powder was wet with water to make a paste which was extruded through a 7/32-inch (0.54 cm) die. The extrudate was cut into 7/32-inch lengths and calcined for 4 hours at 500° C. Using the laboratory reactor as set forth in Example 2 above, the catalyst was contacted with a hydrocarbon-air mixture containing 1.5 mole percent butane at a space velocity of 1420 cc/cc/hour. The yield of maleic anhydride was 51.0% after 116 hours at 415° C. At a temperature of 407° C. the maleic anhydride yield was 48.5% after 97 hours.

In the above Examples, yields of maleic anhydride are reported for that temperature where the particular catalyst gives the maximum yield and for the time period where uniform yield is obtained.

The improvement of catalysts made in accordance with this invention is readily apparent from a comparison of the maleic anhydride yield shown in the above Examples and summarized below:

| Preparation/ Example | Reducing Agent Acid | Temp. °C. | Time Hours | Yield % |
|---|---|---|---|---|
| This invention/2 | Phosphorous | 404 | 103 | 52.3 |
| No intermediate/3 | Phosphorous | 404 | 210 | 49.1 |
| No intermediate/3 | Phosphorous | 412 | 216 | 51.1 |
| No precursor/4 | Oxalic | 416 | 42 | 39.0 |
| No intermediate/6 | Hydrochloric | 438 | 130 | 45.6 |
| No intermediate/7 | Phosphorous | 407 | 97 | 48.5 |
| No intermediate/7 | Phosphorous | 415 | 116 | 51.0 |

Thus it is apparent catalysts prepared according to this invention exhibit about 15 percent better yield of maleic anhydride from butane than catalysts made using the prior art technique and hydrochloric acid as the vanadium reducing agent. Also, the formation of the intermediate compounds exhibits a maleic anhydride yield improvement of 2 to 8 percent. Those skilled in the art will readily recognize that even a 1 percent yield improvement in a chemical process is economically attractive to and continuously sought by industry for reducing cost and raw material requirements.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. As an example, it is known that small amounts of other elements when added to a phosphorus-vanadium-oxygen catalyst may improve the yield of maleic anhydride or may be added to the catalyst to give other desirable properties to the catalyst. Accordingly, modifications are contemplated which can be made without departing from the spirit of the described invention.

What is claimed is:

1. A method of preparing a catalyst which comprises:
   (A) bringing together in a reaction zone a phosphorus compound and a vanadium compound in a phosphorus to vanadium atom ratio between about 0.8:1 and about 1.5:1 under acidic solutions in the absence of hydrogen halide to provide at least 50 atom percent tetravalent vanadium and to form a phosphorus-vanadium-oxygen complex;
   (B) heating the said complex at a temperature between about 60° C. and about 120° C. for a period of time sufficient to form and precipitate an oxide compound which comprises phosphorus, vanadium and oxygen wherein the phosphorus to vanadium atom ratio is between about 0.8:1 and about 1.5:1 and having major X-ray diffraction peaks of:

| d-spacing |
| --- |
| 6.70 |
| 5.68 |
| 3.34 |
| 3.16 |
| 3.09 | in a precipitant comprising water;

(C) heating said composition in a liquid comprising water at a temperature between about 130° C. and about 170° C. for a period of 2-6 hours to form a catalyst precursor;

(D) drying the catalyst precursor;

(E) calcining the catalyst precursor at a temperature between about 300° C. and about 600° C.

2. A method of claim 1 wherein the phosphorus to vanadium atom ratio in the complex is between about 1:1 and 1.2:1.

3. A method of claim 1 wherein the complex is heated at a temperature between about 90° C. and about 100° C. for at least about 24 hours to form and precipitate said oxide compound.

4. A method of claim 1 wherein said complex is heated at a temperature between about 90° C. and about 100° C. for a period of time between about 48 hours and about 72 hours to form and precipitate said oxide compound.

5. A method of claim 1 wherein said phosphorus compound and vanadium compound are brought together in an aqueous acidic medium in said reaction zone.

6. The method of claim 1 wherein said step (A) is conducted in the presence of a mild reducing agent for the vanadium.

7. The method of claim 6 wherein said reducing agent is oxalic acid, phosphorous acid or formaldehyde.

8. A method of claim 7 wherein said phosphorus to vanadium atom ratio is between about 1:1 and about 1.2:1, said complex is heated at a temperature between about 90° C. and about 100° C. for a period of time between about 24 hours and about 72 hours to form and precipitate said oxide compound.

* * * * *